United States Patent
Yin

(10) Patent No.: US 9,781,927 B2
(45) Date of Patent: Oct. 10, 2017

(54) MICROBICIDAL COMPOSITION

(71) Applicant: Dow Global Technologies LLC, Midland, MI (US)

(72) Inventor: Bei Yin, Phoenixville, PA (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 12 days.

(21) Appl. No.: 15/016,685

(22) Filed: Feb. 5, 2016

(65) Prior Publication Data

US 2017/0223954 A1   Aug. 10, 2017

(51) Int. Cl.
| | | |
|---|---|---|
| *A01N 35/00* | (2006.01) | |
| *A01N 35/02* | (2006.01) | |
| *A01N 31/02* | (2006.01) | |
| *C02F 1/50* | (2006.01) | |
| *A01N 25/30* | (2006.01) | |

(52) U.S. Cl.
CPC .............. *A01N 35/02* (2013.01); *A01N 25/30* (2013.01); *A01N 31/02* (2013.01); *C02F 1/50* (2013.01); *C02F 2303/04* (2013.01)

(58) Field of Classification Search
CPC ...................................................... A01N 35/00
See application file for complete search history.

(56) References Cited

U.S. PATENT DOCUMENTS 4,295,932 A   10/1981   Pocius

FOREIGN PATENT DOCUMENTS

| WO | WO2008088647 A1 * | 7/2008 |
| WO | WO2014154946 A1 * | 10/2014 |

OTHER PUBLICATIONS

HealthyPools.org. "Pool Treatment 101: Introduction to Chlorine Sanitizing." © 2016. Available from: < http://www.healthypools.org/wp-content/themes/healthypools/pdfs/swim_pool_101.pdf >.*

* cited by examiner

*Primary Examiner* — Noble Jarrell
*Assistant Examiner* — John S Kenyon
(74) *Attorney, Agent, or Firm* — Tifani M. Edwards

(57) ABSTRACT

A synergistic microbicidal composition comprising a non-ionic surfactant and glutaraldehyde and a method for inhibiting the growth of microorganisms in an aqueous medium.

6 Claims, No Drawings

MICROBICIDAL COMPOSITION

This invention relates to microbicidal compositions containing glutaraldehyde and a surfactant.

A composition containing 5-chloro-2-methylisothiazolin-3-one, 2-methylisothiazolin-3-one and a nonionic dispersant is disclosed in U.S. Pat. No. 4,295,932. The composition contains a 3:1 mixture of 5-chloro-2-methylisothiazolin-3-one and 2-methylisothiazolin-3-one, and a copolymer of ethylene oxide and propylene oxide. However, there is a need for combinations of microbicides having synergistic activity against various strains of microorganisms to provide effective control of the microorganisms. Moreover, there is a need for such combinations containing lower levels of individual microbicides for environmental and economic benefit. The problem addressed by this invention is to provide such synergistic combinations of microbicides.

The present invention is directed to a synergistic microbicidal composition comprising: (a) a nonionic surfactant with structure:

$$R^2O(CH_2CH(CH_3)O)_3(CH_2CH_2O)_7H \quad \text{(Surf. A)}$$

where $R^2$ is a mixture of $C_8$-$C_{14}$ linear alkyl groups; and (b) glutaraldehyde; wherein a weight ratio of the glutaraldehyde to nonionic surfactant is from 17:1 to 1:4.

The present invention is further directed to a synergistic microbicidal composition comprising: (a) a nonionic surfactant with structure:

$$R^2O(CH_2CH(CH_3)O)_3(CH_2CH_2O)_5H \quad \text{(Surf. B)}$$

where $R^2$ is a mixture of $C_8$-$C_{14}$ linear alkyl groups; and (b) glutaraldehyde; wherein a weight ratio of glutaraldehyde to nonionic surfactant is from 17:1 to 4:1.

The present invention is further directed to a synergistic microbicidal composition comprising: (a) a nonionic surfactant with structure:

$$R^2O(CH_2CH(CH_3)O)_3(CH_2CH_2O)_{13}H \quad \text{(Surf. C)}$$

where $R^2$ is a mixture of $C_8$-$C_{14}$ linear alkyl groups; and (b) glutaraldehyde; wherein a weight ratio of glutaraldehyde to nonionic surfactant is from 8:1 to 1:1.

The present invention is further directed to methods for controlling the growth of microorganisms in aqueous media by adding to an aqueous medium a nonionic surfactant as described herein and glutaraldehyde in the ratios described herein.

As used herein, the following terms have the designated definitions, unless the context clearly indicates otherwise. The term "glutaraldehyde" refers to glutaraldehyde, (1,5-pentanedial) CAS No. 111-30-8. The term "microbicide" refers to a compound capable of controlling the growth of or controlling the growth of microorganisms; microbicides include bactericides, fungicides viricides, archaeacides and algaecides. The term "microorganism" includes, for example, fungi (such as yeast and mold), bacteria, virus, archaea and algae. The following abbreviations are used throughout the specification: ppm=parts per million by weight (weight/weight), mL=milliliter. Unless otherwise specified, temperatures are in degrees centigrade (° C.), references to percentages are percentages by weight (wt %) and amounts and ratios are on an active ingredient basis, i.e., total weight of glutaraldehyde and the nonionic surfactant. Numbers of polymerized units of propylene oxide or ethylene oxide are number averages.

The present invention comprises a composition comprising: (a) a nonionic surfactant with structure:

$$R^2O(CH_2CH(CH_3)O)_3(CH_2CH_2O)_7H$$

where $R^2$ is a mixture of $C_8$-$C_{14}$ linear alkyl groups; and (b) glutaraldehyde; has a weight ratio of the glutaraldehyde to nonionic surfactant is from 17:1 to 1:4, alternatively 17.1:1 to 1:3.4.

The invention further comprises a synergistic microbicidal composition comprising: (a) a nonionic surfactant with structure:

$$R^2O(CH_2CH(CH_3)O)_3(CH_2CH_2O)_5H$$

where $R^2$ is a mixture of $C_8$-$C_{14}$ linear alkyl groups; and (b) glutaraldehyde; has a weight ratio of glutaraldehyde to nonionic surfactant is from 17:1 to 3:1, alternatively 17.1:1 to 3.4:1.

The synergistic microbicidal composition comprising: (a) a nonionic surfactant with structure:

$$R^2O(CH_2CH(CH_3)O)_3(CH_2CH_2O)_{13}H$$

where $R^2$ is a mixture of $C_8$-$C_{14}$ linear alkyl groups; and (b) glutaraldehyde; has a weight ratio of glutaraldehyde to nonionic surfactant is from 8:1 to 1:1.

The present invention is further directed to a method for inhibiting the growth of bacteria, preferably anaerobic sulfate-reducing bacteria, in an aqueous medium by adding: (a) a nonionic surfactant with structure:

$$R^2O(CH_2CH(CH_3)O)_3(CH_2CH_2O)_7H$$

where $R^2$ is a mixture of $C_8$-$C_{14}$ linear alkyl groups; and (b) glutaraldehyde; wherein a weight ratio of the glutaraldehyde to nonionic surfactant is from 17:1 to 1:4, alternatively 17.1:1 to 1:3.4.

The present invention is further directed to a method for inhibiting the growth of bacteria, preferably anaerobic sulfate-reducing bacteria, in an aqueous medium by adding: (a) a nonionic surfactant with structure:

$$R^2O(CH_2CH(CH_3)O)_3(CH_2CH_2O)_5H$$

where $R^2$ is a mixture of $C_8$-$C_{14}$ linear alkyl groups; and (b) glutaraldehyde; wherein a weight ratio of glutaraldehyde to nonionic surfactant is from 17:1 to 3:1, alternatively 17.1:1 to 3.4:1.

The present invention is further directed to a method for inhibiting the growth of bacteria, preferably anaerobic sulfate-reducing bacteria, in an aqueous medium by adding (a) a nonionic surfactant with structure:

$$R^2O(CH_2CH(CH_3)O)_3(CH_2CH_2O)_{13}H$$

where $R^2$ a mixture of $C_8$-$C_{14}$ linear alkyl groups; and (b) glutaraldehyde; wherein a weight ratio of glutaraldehyde to nonionic surfactant is from 8:1 to 1:1.

The present invention is further directed to a method for inhibiting the growth of bacteria, preferably facultative bacteria, in an aqueous medium by adding (a) a nonionic surfactant with structure:

$$R^2O(CH_2CH(CH_3)O)_3(CH_2CH_2O)_yH$$

where $R^2$ a mixture of $C_8$-$C_{14}$ linear alkyl groups and y is 3, 5, 7, or 13; and (b) glutaraldehyde; wherein a weight ratio of glutaraldehyde to nonionic surfactant is from 17:1 to 1:1, alternatively 17.1:1 to 1:1.

$R^2$ is a mixture of $C_8$-$C_{14}$ linear alkyl groups. Preferably, the $C_8$-$C_{14}$ linear alkyl groups comprise from 50 to 85 wt % $C_8$-$C_{10}$ linear alkyl groups and 15 to 50 wt % $C_{12}$-$C_{14}$ linear alkyl groups, preferably from 60 to 75 wt % $C_8$-$C_{10}$ linear alkyl groups and 25 to 40 wt % $C_{12}$-$C_{14}$ linear alkyl groups, preferably about 70 wt % $C_8$-$C_{10}$ linear alkyl groups and about 30 wt % $C_{12}$-$C_{14}$ linear alkyl groups. Preferably, the linear alkyl groups are derived from seed oil.

Preferably, each of the compositions is substantially free of microbicides other than the nonionic surfactant and glutaraldehyde, i.e., it has less than 1 wt % of microbicides other than the nonionic surfactant and glutaraldehyde based on total weight of active ingredients, preferably less than 0.5 wt %, preferably less than 0.2 wt %, preferably less than 0.1 wt %. Preferably, when the nonionic surfactant and glutaraldehyde are added to an aqueous medium, the medium is substantially free of other microbicides, i.e., it has less than 1 wt % of microbicides other than the nonionic surfactant and glutaraldehyde based on total weight of active ingredients, preferably less than 0.5 wt %, preferably less than 0.2 wt %, preferably less than 0.1 wt %.

The compositions of this invention may contain other ingredients, e.g., defoamers and emulsifiers. The microbicidal compositions of the present invention can be used to inhibit the growth of microorganisms or higher forms of aquatic life (such as protozoans, invertebrates, bryozoans, dinoflagellates, crustaceans, mollusks, etc) by introducing a microbicidally effective amount of the compositions into an aqueous medium subject to microbial attack. Suitable aqueous media are found in, for example: petroleum processing fluids; fuel; oil and gas field functional fluids, such as injection fluids, hydraulic fracturing fluids, produced fluids and drilling mud, completion and workover fluids; oil and gas pipelines, separation, refining, transportation, and storage system; industrial process water; electrocoat deposition systems; cooling towers; air washers; gas scrubbers; mineral slurries; wastewater treatment; ornamental fountains; reverse osmosis filtration; ultrafiltration; ballast water; evaporative condensers; heat exchangers; pulp and paper processing fluids and additives; starch; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners; cosmetics; toiletries; shampoos; soaps; personal care products such as wipes, lotions, sunscreen, conditioners, creams, and other leave-on applications; detergents; industrial cleaners; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; agriculture adjuvant preservation; surfactant preservation; medical devices; diagnostic reagent preservation; food preservation, such as plastic or paper food wrap; food, beverage, and industrial process pasteurizers; toilet bowls; recreational water; pools; and spas.

The specific amount of the microbicidal compositions of this invention necessary to inhibit or control the growth of microorganisms in an application will vary. Typically, the amount of the composition of the present invention is sufficient to control the growth of microorganisms if it provides from 1 to 5000 ppm (parts per million) active ingredients of the composition. It is preferred that the active ingredients (i.e., nonionic surfactant and glutaraldehyde) of the composition be present in the medium to be treated in an amount of at least 10 ppm, preferably at least 100 ppm, preferably at least 200 ppm. It is preferred that the active ingredients of the composition be present in the locus in an amount of no more than 5000 ppm, preferably no more than 2000 ppm, preferably no more than 1000 ppm, preferably no more than 500 ppm, preferably no more than 300 ppm, preferably no more than 200 ppm. In a method of this invention, a composition is treated to control microbial growth by adding, together or separately, the nonionic surfactant and glutaraldehyde, in amounts that would produce the concentrations indicated above.

EXAMPLES

Surfactants and biocides were evaluated for synergy by determining the synergy index (S.I.) of the combination. Synergy index was calculated based the concentration required to achieve a certain level of bacterial kill when the two antimicrobial compounds (A and B) alone and in combinations. The tests organisms were anaerobic sulfate-reducing bacteria (*Desulfovibrio longus* ATCC #51456), facultative bacteria *Pseudomonas aeruginosa* ATCC #10145 and *Staphylococcus aureus* ATCC #6538,

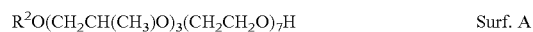
$$R^2O(CH_2CH(CH_3)O)_3(CH_2CH_2O)_7H \qquad \text{Surf. A}$$

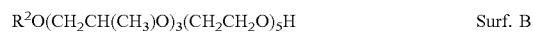
$$R^2O(CH_2CH(CH_3)O)_3(CH_2CH_2O)_5H \qquad \text{Surf. B}$$

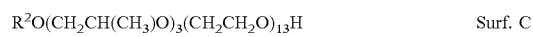
$$R^2O(CH_2CH(CH_3)O)_3(CH_2CH_2O)_{13}H \qquad \text{Surf. C}$$

where $R^2$ is a mixture of $C_8$-$C_{14}$ linear alkyl groups.

Example 1. Synergistic Effect of Glutaraldehyde and Surf A-C Against Anaerobic Sulfate-Reducing Bacteria Inside an anaerobic chamber (Bactron anaerobic chamber), a deoxygenated sterile salt solution (3.1183 g of NaCl, 1.3082 mg of $NaHCO_3$, 47.70 mg of KCl, 72.00 mg of $CaCl_2$, 54.49 mg of $MgSO_4$, 172.28 mg of $Na2SO_4$, 43.92 mg of $Na_2CO_3$ in 1 L water) was inoculated with *Desulfovibrio longus* ATCC 51456 to a final bacterial concentration of $10^6$ to $10^7$ CFU/mL. Aliquots of this cell suspension were then treated with glutaraldehyde, and each of Surf A-C at selected active concentrations. After incubation at 35° C. for 2 hours, viable bacteria in the aliquots were enumerated using serial dilution method. Synergistic combinations and their biocidal efficacy as well as Synergy Index were summarized in Table 1 to Table 3.

The test results for demonstration of synergy of the combinations are shown in the tables below. Each table shows the results for combinations of two components against the microorganisms tested with incubation times; the end-point activity in ppm measured by the level of kill for compound A alone (CA), for component B alone (CB), and the mixture (Ca) and (Cb); the calculated SI value; and the range of synergistic ratios for each combination tested. SI is calculated as follows:

$$Ca/CA + Cb/CB = \text{Synergy Index (“SI”)}$$

Wherein:
Ca=Concentration of biocide A required to achieve a certain level of bacterial kill when used in combination with B
CA=Concentration of biocide A required to achieve a certain level of bacterial kill when used alone
Cb=Concentration of biocide B required to achieve a certain level of bacterial kill when used in combination with A
CB=Concentration of biocide B required to achieve a certain level of bacterial kill when used alone
When the sum of Ca/CA and Cb/CB is greater than one, antagonism is indicated. When the sum is equal to one, additivity is indicated, and when less than one, synergism is demonstrated.

TABLE 1

Biocidal efficacy of glutaraldehyde (Glut) and Surf. A against anaerobic sulfate-reducing bacteria, and Synergy Index

| Active weight ratio of Glut:Surf. A | Concentration (active ppm) for 99.99% bacterial kill in 2 hours | | Synergy Index |
|---|---|---|---|
| | Glut | Surf. A | |
| 1:0 | 13.2 | 0.0 | |
| 17.1:1 | 8.8 | 0.5 | 0.67 |
| 11.4:1 | 8.8 | 0.8 | 0.67 |
| 3.4:1 | 8.8 | 2.6 | 0.69 |
| 1:3.4 | 8.8 | 29.6 | 0.96 |
| 0:1 | 0.0 | >100 | |

TABLE 2

Biocidal efficacy of glutaraldehyde (Glut) and Surf C against anaerobic sulfate-reducing bacteria, and Synergy Index

| Active weight ratio of Glut:Surf C | Concentration (active ppm) for complete bacterial kill in 2 hours | | Synergy Index |
|---|---|---|---|
| | Glut | Surf C | |
| 1:0 | 29.6 | 0.0 | |
| 8:1 | 13.2 | 1.6 | 0.46 |
| 6.7:1 | 13.2 | 2.0 | 0.46 |
| 5:1 | 19.8 | 4.0 | 0.71 |
| 3:1 | 13.2 | 4.4 | 0.49 |
| 1:1 | 13.2 | 13.2 | 0.58 |
| 0:1 | 0.0 | >100 | |

TABLE 3

Biocidal efficacy of glutaraldehyde (Glut) and Surf. B against anaerobic sulfate-reducing bacteria, and Synergy Index

| Active weight ratio of Glut:Surf. B | Concentration (active ppm) for more than 99.999% bacterial kill in 2 hours | | Synergy Index |
|---|---|---|---|
| | Glut | Surf. B | |
| 1:0 | 29.6 | 0.0 | |
| 17.1:1 | 19.8 | 1.2 | 0.68 |
| 11.4:1 | 19.8 | 1.7 | 0.68 |
| 7.6:1 | 19.7 | 2.6 | 0.69 |
| 3.4:1 | 19.7 | 5.9 | 0.73 |
| 0:1 | 0.0 | >100 | |

Example 2. Synergistic Effect of Glutaraldehyde and Surf. B Against Bacteria

Sterile 0.85% NaCl solution was inoculated with approximately $10^7$ CFU/mL of *Pseudomonas aeruginosa* ATCC 10145 and *Staphylococcus aureus* ATCC 6538. Aliquots of the cell suspension were then treated with glutaraldehyde, and Surfs. A-D at selected concentrations. After incubating at 37° C. for 2 hr, viable bacteria in the aliquots were enumerated using serial dilution method. Synergistic combinations and their biocidal efficacy as well as Synergy Index* were summarized in Table 4.

TABLE 4

Biocidal efficacy of glutaraldehyde (Glut), Surf. B against aerobic bacteria, and Synergy Index

| Active weight ratio of Glut:Surf. B | Concentration (active ppm) for more than 99.999% bacterial kill in 2 hours | | Synergy Index |
|---|---|---|---|
| | Glut | Surf. B | |
| 1:0 | 29.6 | 0.0 | |
| 17.1:1 | 19.8 | 1.2 | 0.68 |
| 11.4:1 | 19.8 | 1.7 | 0.68 |
| 7.6:1 | 19.7 | 2.6 | 0.69 |
| 3.4:1 | 19.7 | 5.9 | 0.73 |
| 1:1 | 19.8 | 19.8 | 0.86 |
| 0:1 | 0.00 | >100 | |

The invention claimed is:

1. A synergistic microbicidal composition comprising: (a) a nonionic surfactant with structure:

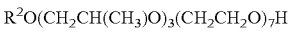

where $R^2$ is a mixture of $C_8$-$C_{14}$ linear alkyl groups; and (b) glutaraldehyde; wherein a weight ratio of the glutaraldehyde to nonionic surfactant is from 17:1 to 1:4.

2. A method for controlling the growth of microorganisms in an aqueous medium; the method comprising adding to the aqueous medium the synergistic microbicidal composition of claim 1.

3. A synergistic microbicidal composition comprising: (a) a nonionic surfactant with structure:

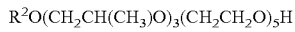

where $R^2$ is a mixture of $C_8$-$C_{14}$ linear alkyl groups; and (b) glutaraldehyde; wherein a weight ratio of glutaraldehyde to nonionic surfactant is from 17:1 to 3:1.

4. A method for controlling the growth of microorganisms in an aqueous medium; the method comprising adding to the aqueous medium the synergistic microbicidal composition of claim 3.

5. A synergistic microbicidal composition comprising: (a) a nonionic surfactant with structure:

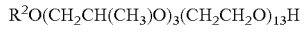

where $R^2$ is a mixture of $C_8$-$C_{14}$ linear alkyl groups; and (b) glutaraldehyde; wherein a weight ratio of glutaraldehyde to nonionic surfactant is from 8:1 to 1:1.

6. A method for controlling the growth of microorganisms in an aqueous medium; the method comprising adding to the aqueous medium the synergistic microbicidal composition of claim 5.

* * * * *